(12) United States Patent
Peters et al.

(10) Patent No.: US 7,238,246 B2
(45) Date of Patent: Jul. 3, 2007

(54) PROCESS FOR THE FLUSH CONNECTION OF BODIES

(75) Inventors: Ralf-Peter Peters, Bergisch-Gladbach (DE); Wolfgang Stoeters, Muelheim (DE)

(73) Assignee: Boehringer Ingelheim microparts GmbH, Dortmund (DE)

( * ) Notice: Subject to any disclaimer, the term of this patent is extended or adjusted under 35 U.S.C. 154(b) by 0 days.

(21) Appl. No.: 10/157,923

(22) Filed: May 31, 2002

(65) Prior Publication Data

US 2002/0195196 A1    Dec. 26, 2002

(30) Foreign Application Priority Data

Jun. 23, 2001 (DE) ................. 101 30 428

(51) Int. Cl.
*B32B 37/00* (2006.01)
(52) U.S. Cl. .............. 156/83; 156/292; 156/308.2; 156/308.6; 264/343; 427/307
(58) Field of Classification Search ............... 156/83, 156/308.2, 308.6, 292; 264/343; 427/307
See application file for complete search history.

(56) References Cited

U.S. PATENT DOCUMENTS

| 2,521,470 | A | * | 9/1950 | Matheson ............... 156/308.6 |
| 3,471,353 | A | * | 10/1969 | Rasmussen ............... 156/289 |
| 3,589,959 | A | | 6/1971 | Sander et al. |
| 3,684,553 | A | * | 8/1972 | Van Dyk .................. 427/444 |
| 3,853,659 | A | * | 12/1974 | Rhodes ..................... 156/181 |
| 4,762,580 | A | * | 8/1988 | Robertson .................. 156/83 |
| 5,126,022 | A | | 6/1992 | Soane et al. |
| 5,376,252 | A | | 12/1994 | Ekstrom et al. |
| 5,571,410 | A | | 11/1996 | Swedberg et al. |
| 5,605,613 | A | | 2/1997 | Shieh |
| 5,750,015 | A | | 5/1998 | Soane et al. |
| 5,858,188 | A | | 1/1999 | Soane et al. |
| 5,935,401 | A | | 8/1999 | Amigo |
| 6,054,034 | A | | 4/2000 | Soane et al. |
| 6,056,860 | A | | 5/2000 | Amigo |
| 6,093,296 | A | | 7/2000 | Soane et al. |
| 6,176,962 | B1 | | 1/2001 | Soane et al. |

FOREIGN PATENT DOCUMENTS

| DE | 1 153 885 | 9/1963 |
| DE | 1 679 900 | 4/1971 |
| DE | 39 26 567 | 3/1990 |
| DE | 198 51 644 | 8/1999 |
| WO | WO 98/45693 | 10/1998 |

* cited by examiner

*Primary Examiner*—John L. Goff
(74) *Attorney, Agent, or Firm*—Oblon, Spivak, McClelland, Maier & Neustadt, P.C.

(57) ABSTRACT

In the swell-welding according to the invention of two bodies, of which at least one body consists of plastic, the connection surface of the plastic body is firstly exposed to a gas which contains the vapor of a swelling agent for the plastic. The plastic body reversibly swollen at the surface is welded to the other body by pressing onto one another, and the pressed-together bodies are conditioned. In all process steps, the temperature of the bodies to be connected is below the glass transition temperature of the plastic. No auxiliary substance remains in the welded body. The flush connection produced by swell welding is durable and strong.

11 Claims, 1 Drawing Sheet

PROCESS FOR THE FLUSH CONNECTION OF BODIES

The invention relates to a process for the flush connection of bodies, at least one of which is a body consisting of plastic.

The invention has the purpose of connecting two bodies to one another in a flush and non-detachable manner, with any microstructures present on the surface to be connected remaining unchanged.

WO 98/45693 discloses processes for the flush connection of bodies, of which at least one base body consisting of plastic contains microchannels which are covered by the cover body in a flush connection. The surfaces of the two bodies to be connected to one another are generally flat. The two bodies can be pressed against one another and welded to one another by warming or by means of ultrasound. The temperature used is from 2° C. to 5° C. above the glass transition temperature of the plastic.

Furthermore, a film-like layer of a flowable adhesive is applied to one side, preferably of the non-microstructured cover body, and converted into a non-flowable state. The coated surface of the cover body is pressed onto the base body, and the adhesive is cured to completion. After the curing process, a body provided with covered microchannels is obtained, in which the base body is durably held together with the cover body by means of the adhesive layer between the surfaces of the two bodies lying on one another.

The adhesives used are hot-melt adhesives, adhesive curable substances, elastomeric adhesives, adhesive natural or synthetic rubber, polyurethanes, polysulphides or silicones. The elastomeric adhesives are in the form of a solution, emulsion or preparation of two reactive components. The adhesives are contact adhesives or two-component adhesives. The two-component adhesives are cured by heating or by polymerization. In this case, a photoinitiator or thermal initiator is used if necessary. The reaction is carried out with exposure of the joined surface of the base body and of the cover body to light or heat.

In the processes of the prior art, either an adhesive is used as auxiliary substance, which remains in the interlayer between the two bodies bonded to one another, or the plastic used for the base body and/or the cover body is warmed to a temperature which is above the glass transition temperature of the plastic.

The object is therefore to indicate a process for the flush connection of two bodies in which at least one of the bodies consists of plastic. The aim is to connect the two bodies durably to one another without using an auxiliary which remains between the connected bodies, for example an adhesive, which is in the form of a layer between the surfaces of the two bodies lying one on top of the other. The surfaces of the two bodies to be connected to one another may, if desired, be changed only temporarily and reversibly. The bodies may only be warmed to a temperature at which they remain virtually unchanged.

The object is achieved in accordance with the invention by a process having the following characterizing features:

A vapour-containing gas is prepared which consists of a carrier gas and the vapour of a liquid which is a swelling agent for the plastic.

At least the connection surface of the at least one plastic body is exposed to the gas containing swelling agent vapour, causing the connection surface to be partially swollen in a layer close to the surface.

The at least one body made of plastic has a temperature below its glass transition temperature during the treatment in the gas containing swelling agent vapour.

The plastic body swollen at the surface is removed from the gas containing swelling agent vapour and (preferably immediately) welded to the other body by pressing onto one another at a temperature below its glass transition temperature.

The bodies welded to one another are conditioned at a temperature below the glass transition temperature of the plastic.

This process is carried out, for example, using an apparatus which essentially consists of the following devices: a container for the carrier gas, a thermostatted liquid container, a pre-cooler, a deposition chamber, a main cooler, a condensate trap, a press device and an oven.

The process according to the invention is carried out as follows: the liquid container contains the liquid swelling agent for the plastic. The temperature of the liquid is held at a pre-specified value by means of a thermostat. The carrier gas is passed into the liquid phase inside the liquid container and flows through the liquid. The temperature of the liquid in the liquid container can be between 15° C. and about 10 degrees below the boiling point of the liquid. The carrier gas can have a temperature of from 10° C. to 110° C. before loading with liquid vapour.

The gas containing swelling agent vapour is taken from the liquid container and passed through a pre-cooler. In the pre-cooler, the gas containing swelling agent vapour is cooled to a constant temperature. The temperature of the gas containing swelling agent vapour can be from 15° C. to 110° C.

This gas containing swelling agent vapour is passed through the deposition chamber and subsequently through the main cooler, in which the majority of the swelling agent vapour is separated from the gas containing swelling agent vapour by condensation and can be collected in the condensate trap. The condensate can be fed back into the liquid container.

The gas discharged from the condensate trap, which now only contains a little swelling agent vapour, can be burnt if a combustible swelling agent is used. If desired, the remainder of the swelling agent vapour can be removed from the carrier gas by means of an absorber. The carrier gas freed from swelling agent vapour can escape or be collected. On the other hand, the gas containing swelling agent vapour which is discharged from the deposition chamber can be fed back into the liquid container either directly or after passing through the main cooler.

The at least one body made of plastic is introduced into the deposition chamber, in which preferably only the body surface intended for the connection is exposed to the gas containing swelling agent vapour. The gas containing swelling agent vapour has a temperature of from 15° C. to 60° C. The proportion of swelling agent vapour is from $1\times10^{-6}$ to $5\times10^{-2}$ (from 1 ppm to 5%). The at least one body made of plastic can have a temperature of from 30° C. below to 10° C. above the temperature of the gas containing swelling agent vapour during the treatment in the gas containing swelling agent vapour. The treatment time of the at least one body made of plastic in the deposition chamber can be from 0.5 seconds to 180 seconds.

The swelling agent diffuses out of the gas phase into the plastic body. The plastic body swells in its layer close to the surface due to the swelling agent diffusing in. Due to the swelling, the plastic body becomes reversibly thicker by a few microns. In the swollen layer, the mobility of molecules in the surface of the plastic body is increased. The diffusion layer can be a few tens of microns thick, and is not sharply delimited in the interior of the plastic body. The thickness of the diffusion layer can be adjusted through the way in which the process is carried out. The main process parameters for this purpose are

- the temperature of the liquid swelling agent in the liquid container, the temperature of the carrier gas before entry into the liquid container and the residence time of the carrier gas passed through the liquid swelling agent in the liquid container;
- the temperature of the gas containing swelling agent vapour on entry into the deposition chamber;
- the temperature of the plastic body in the deposition chamber;
- the temperature difference between the gas containing swelling agent vapour and the plastic body;
- the residence time of the plastic body in the deposition chamber;
- the type of plastic;
- the type of swelling agent.

The body swollen at the surface is preferably placed into the press device outside the deposition chamber and pressed together with the other body. The two bodies are connected to one another in a flush manner. The bodies to be connected can be welded to one another at a pressure of from 10 N/cm$^2$ to 500 N/cm$^2$ for a period of from 3 seconds to 120 seconds. The pressure is applied uniformly over the surface to be welded.

The two welded bodies are conditioned in the oven— without or with an applied pressure—with the swelling agent that has penetrated into the at least one plastic body being expelled. The welded bodies can be conditioned at a temperature of from 30° C. to 3 degrees below the glass transition temperature of the plastic for a period of from 10 minutes to 60 minutes under a mechanical pressure of from 5 N/cm$^2$ to 50 N/cm$^2$ or for a period of from 10 minutes to 180 minutes without mechanical pressure.

Rapid expulsion of the swelling agent from the swollen layer, for example by conditioning at elevated temperature, with maintenance of a mechanical pressure gives strong and durable joins. Slow expulsion of the swelling agent, for example by allowing the connected bodies to lie at ambient temperature, gives less strong and less durable joins.

It has proven sufficient in many cases for flush connection of two plastic bodies to treat only the connection surface of the first plastic body with gas containing swelling agent vapour in accordance with the process according to the invention. On the other hand, it may be advantageous to treat the connection surfaces of both plastic bodies to be connected with gas containing swelling agent vapour in accordance with the process according to the invention.

The at least one body made of plastic may consist, for example, of polymethyl methacrylate (PMMA), polycarbonate, polyether sulphone or polystyrene.

Suitable swelling agents are solvents for the plastic and other swelling agents. The following are suitable:

- saturated hydrocarbons, such as hexane, heptane, cyclohexane,
- alcohols, such as methanol, ethanol, isopropanol, amyl alcohol, cyclohexanol,
- aldehydes, such as acetaldehyde, benzaldehyde,
- ketones, such as acetone, methyl ethyl ketone, diethyl ketone, cyclohexanone,
- halogenated hydrocarbons, such as methylene chloride, dichloromethane, trichloromethane, tetrachloromethane, ethylene chloride, dichloroethane, trichloroethane, tetrachloroethane, amyl chloride,
- ethers, such as diethyl ether, diisopropyl ether
- esters, such as methyl acetate, ethyl acetate, propyl acetate, butyl acetate, amyl acetate,
- aromatic hydrocarbons and substituted aromatic hydrocarbons, such as benzene, toluene, xylene, styrene, isopropylbenzene, dichlorobenzene,
- and carbon disulphide, dioxane, N-methylpyrrolidone, tetrahydrofuran, tetrahydronaphthalene and others.

A suitable carrier gas is, for example, nitrogen, carbon dioxide, argon, neon or helium. For safety reasons, a non-combustible carrier gas or an oxygen-free gas is preferred. A combustible carrier gas or an oxygen-containing carrier gas, for example air, is likewise suitable given appropriate safety precautions.

Any moisture present in the carrier gas or any water present in the swelling agent should be noted. The presence of water or water vapour can affect the concentration of the swelling agent vapour in the carrier gas and have an effect on the swelling process.

The process according to the invention can be used for the flush connection of bodies which both preferably consist of the same plastic, and for the flush connection of bodies of which one body consists of plastic and the other, for example, of glass, silicon or metal or another plastic. A smooth surface of the bodies to be connected is more favourable than a rough surface.

The process according to the invention can be carried out discontinuously and applied to individual bodies to be connected in a flush manner, in each case welded under pressure with the aid of a press device. It can furthermore be carried out as a quasi-continuous process or as a continuous process if at least one of the two bodies to be connected in a flush manner is in ribbon-like or taped form.

The process according to the invention is preferably used for the flush connection of bodies of which at least one body is provided with a microstructure. The microstructured body may consist of plastic and can be connected in a flush manner to a non-microstructured body of the same plastic. In this case, the side of the non-microstructured body intended for the flush connection is preferably exposed to the gas containing swelling agent vapour and swollen.

If the microstructured body consists of a non-swellable substance, for example silicon, this body can be connected in a flush manner to another body consisting of plastic after the plastic body has preferably been swollen on the one side by the process according to the invention.

The production of the microstructure is substantially of secondary importance for the process according to the invention. The microstructure can be produced by subtractive structuring, i.e. by imagewise removal of material (for example by imagewise fine-mechanical precision machining or anisotropic etching), by additive structuring, i.e. by imagewise application of material (for example by imagewise deposition of material from the vapour phase or by imagewise electrolytic deposition of metal), or by a combination of the two processes, or by moulding (for example by taking casts from a microstructured mould insert during injection moulding) or by forming (for example by embossing).

The process according to the invention can be used for virtually any microstructures, in particular microstructures having a cavity depth of from 2 μm to 1000 μm and a cavity width of from 2 μm to 500 μm with an aspect ratio (ratio of cavity depth to cavity width) of from 0.05:1 to 100:1, for example for channel-like microstructures or for microstructures in the form of a field comprising columns having a separation of from 2 µm to 1000 µm between two columns and a column height of from 5 µm to 1000 µm on an area of, for example, 100 mm×100 mm, or for hole fields. It is favourable if, in the microstructured region of the microstructure body, the area of the welded regions between the at least one body made of plastic and the other body to be welded thereto is greater than the area of the unwelded regions, and if the welded and unwelded regions are distributed fairly uniformly over the microstructured area.

Microstructures produced by fine-mechanical precision machining in a plastic body are less sensitive to deformation during swelling than microstructured plastic bodies produced by casting from a mould insert, in which internal stresses may be present in the region of the microstructures.

The process according to the invention can be employed both for non-microstructured areas to be connected and for microstructured areas.

The process is not restricted to flat surfaces, but can also be used for curved surfaces which can be brought into flush contact.

The process enables the fabrication of large numbers of connected bodies on use of a continuous oven with temperature-controlled zones.

The process according to the invention has the following advantages:

At the moderately elevated temperature of the body, which is significantly below the melting point, any microstructure present in the surfaces to be connected is only slightly influenced by mechanical pressure, or not at all.

The cross section of covered microchannels is only deformed slightly, or not at all.

Covered microchannels have good fluid properties.

Adhesive or other auxiliary materials, for example adhesion promoters, cannot penetrate into cavities of the microstructure since no auxiliary material is used.

The surfaces of the two bodies lying one on top of the other are virtually in the initial state again after the end of the connection process; they are not permanently changed.

The connected bodies are virtually free from swelling agent.

The connected bodies contain no additional material (for example adhesive or adhesion promoter) in the connection area.

The surface of the two bodies connected by swell welding has high strength.

Bodies connected to one another in a flush manner in accordance with the invention can be used, for example, as microtiter plate for investigation of the action of antibiotics on living cells, or for the separation of cell suspensions, or as channel plate for capillary electrophoresis, or for the production of fluid functional parts, such as valves or reservoirs, or for the hermetic sealing of sensitive components, such as sensors.

The process according to the invention is explained in greater detail with reference to the figures. FIGS. 1 to 4 show bodies in cross section, of which at least one body consists of plastic, and of which one body is microstructured.

Figure 1:
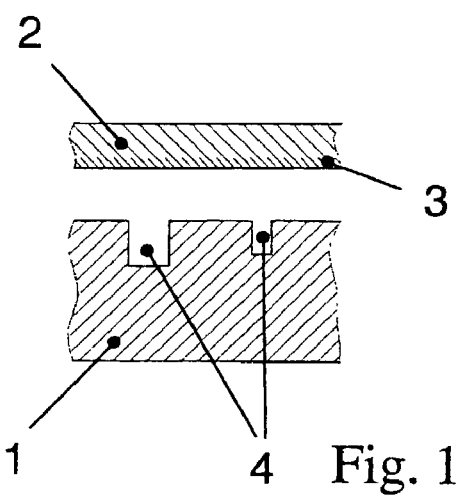
FIG. 1 shows a body provided with microchannels (4) and a non-microstructured plastic body (2) before the welding of these two bodies. The plastic body (2) is swollen on its first side in the layer (3) close to the surface by the action of a gas containing swelling agent vapour.
Figure 2:
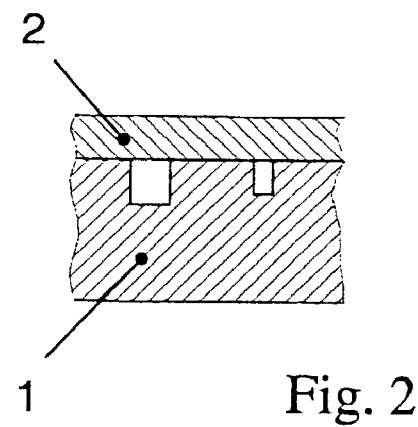
FIG. 2 shows the two bodies (1) and (2) welded to one another in a flush manner. The surface of the body (2) is virtually flat at the points where the microchannels are present in the body (1).
Figure 3:
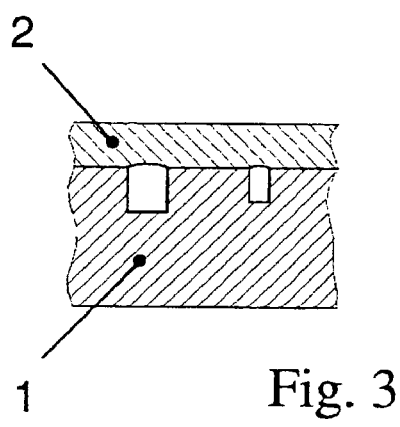
Figure 4:
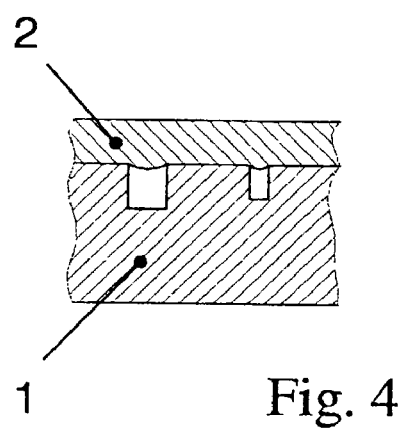

FIGS. 3 and 4 show analogously to FIG. 2 two bodies (1) and (2) connected to one another in a flush manner by swell welding. In both cases, the surface of the body (2) is slightly deformed in the micron region, into the body (2) in FIG. 3 and out of the body (2) in FIG. 4, at the points where the microchannels are present in the body (1). This does not impair the fluid properties of the microchannels.

Figure 5:
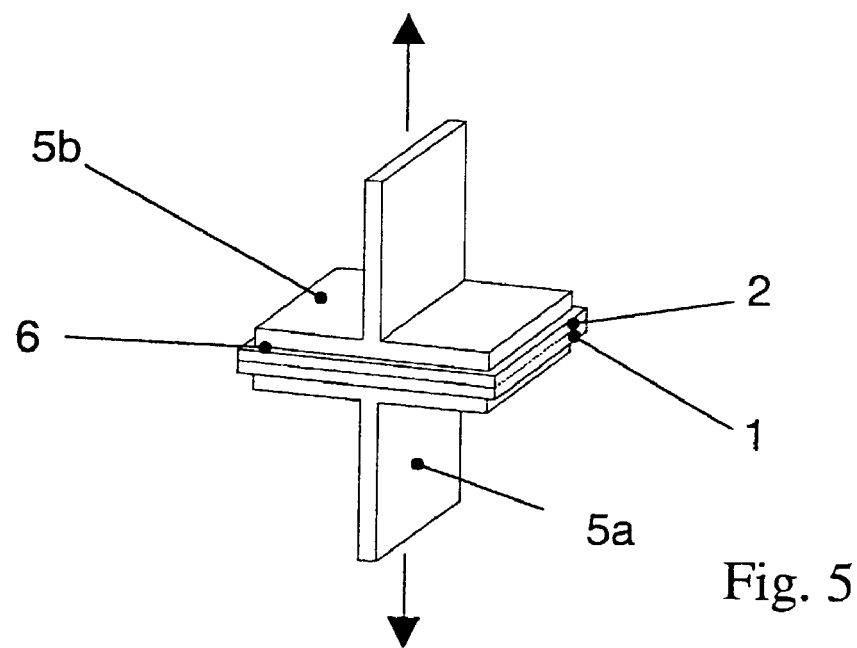

FIG. 5 shows an angled view of an alternative arrangement with which the strength of a body produced by the process according to the invention can be determined. A plurality of bodies each consisting of a square perforated plate of PMMA with a thickness of 2 mm and an area of 22 mm times 22 mm and a non-microstructured plate of PMMA with a thickness of 1 mm swell-welded thereto were produced as described in Example 1. A perforated plate was provided with 16 holes with a diameter of about 2 mm arranged uniformly on the plate, and was provided on the side connected to the other plate with connection channels with a depth of 10 µm and a width of 20 µm between adjacent holes in each case.

For determination of the strength of the plates (1) and (2) swell-welded to one another in a flush manner, a T-shaped holder (5a; 5b) was stuck to each of the two flat sides of the welded body by means of epoxy resin. The first adhesive layer is indicated by (6). On placement of the holder on the perforated plate side, the penetration of epoxy resin into the holes open on one side was prevented. The arms of the T-shaped holder pointing away from the perforated plate were parallel to one another and arranged vertically one above the other. The two arrows indicate the direction of the tensile force.

EXAMPLE 1

Dichloromethane is warmed to 35° C. under ambient pressure and held at this temperature. Nitrogen (at about 20° C.) is flushed through the liquid. The discharged gas containing swelling agent vapour has a temperature of about 33° C.; it is cooled to 27° C. in a pre-cooler.

The gas containing swelling agent vapour at a temperature of 27° C. acts on the side of a non-microstructured body made of PMMA whose temperature is 22° C. for 15 seconds. Through the swelling agent condensed on the surface of the body, which diffuses into the plastic. The surface of this plastic body is swollen in the process.

The second body likewise consists of PMMA and is provided with a channel-like microstructure. The channels have a width of 100 µm, a depth of 20 µm and a length of a few millimeters. The plastic body swollen at the surface on one side is pressed onto the microstructured side of the other body for 25 seconds with a pressure of 50 N/cm$^2$ and held under this pressure, which acts uniformly on the surfaces to be connected. The temperature of the two bodies still pressed together at 50 N/cm$^2$ is raised to 45° C. and held at this temperature for 60 minutes. The dichloromethane which has diffused into the plastic is expelled in the process and can preferably escape via the microstructure channels, which are open at least at one end. Conditioning of the two bodies welded to one another in a flush manner gives the finished body.

EXAMPLE 2

Styrene is warmed to 44° C. under atmospheric pressure and held at this temperature. Nitrogen (at about 20° C.) is flushed through the liquid. The discharged gas containing swelling agent vapour has a temperature of about 41° C.; it is cooled to 36° C. in a pre-cooler.

The gas containing swelling agent vapour at a temperature of 36° C. acts on one side of a non-microstructured plate of polystyrene with a thickness of 1 mm which has a temperature of 31° C. for 30 seconds. The surface of this plastic body is swollen in the process.

The second body consists of a perforated plate made of polystyrene with a thickness of 1 mm which is provided with through-holes with a diameter of 2 mm. The non-microstructured plastic plate swollen at the surface on one side is pressed onto the microstructured side of the perforated plate for 30 seconds at a pressure of 40 N/cm$^2$ and held under this pressure acting uniformly on the surfaces to be connected. The temperature of the two plates still pressed together at 40 N/cm$^2$ is raised to 55° C. and held at this temperature for 45 minutes. The styrene which has diffused into the plastic is expelled in the process. Conditioning of the two bodies welded to one another in a flush manner gives the finished body, which consists of a perforated plate having holes open on one side and a base with a thickness of 1 mm.

EXAMPLE 3

The strength of bodies swell-welded to one another by the process according to the invention is determined as follows using the arrangement shown diagrammatically in FIG. 5.

In each case, a body, consisting of the perforated plate and the non-microstructured plate swell-welded thereto and provided with holders, was clamped into the clamps of a tensile testing machine. A tensile force was applied to the test specimens perpendicularly to the welded surface. In the case of some test specimens, one of the two T-shaped holders stuck on tore off before the two swell-welded bodies separated at their joint surface.

The tensile force acting perpendicularly to the swell-welded surface which had to be applied in order to separate the bodies swell-welded to one another at their joint surface, based on the swell-welded surface of a test specimen (calculated without the cross-sectional surface of all holes and without the longitudinal section areas of the connecting channels), was greater than 120 N/cm$^2$.

The invention claimed is:

1. Process for flush connection of two bodies wherein at least one body consists of a plastic material, and at least one body is provided with a microstructure having a cavity depth of from 2 μm to 1000 μm and a cavity width of from 2 μm to 500 μm and an aspect ratio of from 0.05:1 to 100:1, comprising:

preparing a gas comprising a carrier gas and a vapor of a liquid plastic swelling agent, suitable for swelling the plastic material, wherein the proportion of the swelling agent vapor is from $1\times10^{-6}$ to $5\times10^{-2}$;

exposing a connection surface of the at least one plastic body to the gas to partially swell a layer close to the connection surface during a treatment time of from 0.5 seconds to 180 seconds, wherein the swelling agent diffuses out of the gas phase into the plastic body;

maintaining the plastic body at a temperature below a glass transition temperature of the plastic material while the plastic body is exposed to the gas;

removing the plastic body from the gas;

pressing the plastic body having the swelled layer to the other body to weld the two bodies to one another at a temperature below the glass transition temperature of the plastic material; and conditioning the welded bodies at a temperature below the glass transition temperature of the plastic material.

2. Process according to claim 1, wherein the plastic body is held at a temperature from 30° C. below to 10° C. above a temperature of the gas while the plastic body is exposed to the gas.

3. Process according to claim 1, wherein a temperature of the gas is from 15° C. to 110° C.

4. Process according to claim 1, wherein the bodies are welded to one another at a mechanical pressure of from 10 N/cm$^2$ to 500 N/cm$^2$ for a period of from 3 seconds to 120 seconds.

5. Process according to claim 1, wherein the welded bodies are conditioned at a temperature of from 30° C. to 3 C. below the glass transition temperature of the plastic body for a period of from 10 minutes to 60 minutes under a mechanical pressure of from 5 N/cm$^2$ to 50 N/cm$^2$.

6. Process according to claim 1, wherein the welded bodies are conditioned at a temperature of from 30° C. to 3 C. below the glass transition temperature of the plastic body for a period of from 10 minutes to 180 minutes without application of mechanical pressure.

7. Process according to claim 1, wherein both bodies comprise a plastic material and one of the bodies is provided with a microstructure and the connection surface of the other body is exposed to the gas to partially swell a layer close to the connection surface.

8. Process according to claim 1, wherein the plastic body comprises polymethyl methacrylate, and the liquid plastic swelling agent comprises dichloromethane.

9. Process according to claim 1, wherein the plastic body comprises polystyrene, and the liquid plastic swelling agent comprises styrene.

10. Process according to claim 1, wherein the plastic body comprises polycarbonate, and the liquid plastic swelling agent comprises benzene.

11. Process according to claim 1, wherein the plastic body comprises polyether sulphone, and the liquid swelling agent comprises N-methylpyrrolidone.

* * * * *